United States Patent
Lum et al.

[19]

[11] Patent Number: 6,132,449
[45] Date of Patent: Oct. 17, 2000

[54] EXTRACTION AND TRANSPORTATION OF BLOOD FOR ANALYSIS

[75] Inventors: Paul Lum, Los Altos; Leslie A. Leonard, Portola Valley; Edward D. Verdonk, San Jose; Dominique M. Freeman, Pescadero; Michael Greenstein, Los Altos; Catherine Keely-Templin, Portola Valley, all of Calif.

[73] Assignee: Agilent Technologies, Inc., Palo Alto, Calif.

[21] Appl. No.: 09/264,597

[22] Filed: Mar. 8, 1999

[51] Int. Cl.[7] .................................................. A61B 17/32
[52] U.S. Cl. ........................................... 606/181; 606/182
[58] Field of Search ................................... 606/181, 182, 606/183, 170; 128/765, 763

[56] References Cited

U.S. PATENT DOCUMENTS

| | | | |
|---|---|---|---|
| 3,358,689 | 12/1967 | Higgins | 128/329 |
| 4,109,655 | 8/1978 | Chaconac | 128/253 |
| 4,301,412 | 11/1981 | Hill et al. | 324/442 |
| 4,469,110 | 9/1984 | Slama | 128/770 |
| 4,857,274 | 8/1989 | Simon | 422/72 |
| 4,995,402 | 2/1991 | Smith et al. | 128/771 |
| 5,047,044 | 9/1991 | Smith et al. | 606/182 |
| 5,217,480 | 6/1993 | Haber et al. | 606/182 |
| 5,314,442 | 5/1994 | Morita | 606/182 |
| 5,611,809 | 3/1997 | Marhall et al. | 606/181 |
| 5,624,458 | 4/1997 | Lipscher | 606/181 |
| 5,628,765 | 5/1997 | Morita | 606/182 |
| 5,662,127 | 9/1997 | De Vaughn | 606/181 |

*Primary Examiner*—Michael Buiz
*Assistant Examiner*—Kevin Truong
*Attorney, Agent, or Firm*—Philip S. Yip; Gordon M. Stewart

[57] ABSTRACT

A device for sampling blood from the skin of a patient by puncture. The device includes one or more lancets for lancing the skin and a fluid-conducting plate unit for transporting blood from the lancing wound. The plate unit has one or more channels for conducting fluid to one or more target locations. Preferably there is a first channel for conducting away a first portion of fluid that contains more of a fluid that is emitted initially (initial fluid) from the puncture wound and a second channel for conducting a second portion of fluid that contains less of the initial fluid from the puncture wound. Blood is drawn into the channels by capillary force. The device can be used to lance the skin and obtain a representative sample of blood with relatively simple procedures.

21 Claims, 11 Drawing Sheets

EXTRACTION AND TRANSPORTATION OF BLOOD FOR ANALYSIS

FIELD OF THE INVENTION

The present invention relates to devices for penetrating the skin to extract blood or other fluids, and more particularly, to a skin-pricking device that is capable of transporting fluid from the skin.

BACKGROUND OF THE INVENTION

Medical tests that require a small volume of blood are well known. For example, home test kits for measuring blood sugar levels are utilized by diabetics. These test kits require that a drop of blood be placed on a test strip that is then inserted into a measurement apparatus that displays the glucose concentration in the blood sample. To obtain the drop of blood, the user is supplied with a lancet device, which makes a skin prick, typically in the user's finger. Inserting the needle or lancet into the skin produces pain in the skin tissue. In patients such as diabetics, who have to sample their blood often, any excessive pain or tissue trauma is a disincentive to comply with the blood sampling routine. It would be advantageous to minimize the physical discomfort associated with this skin prick to obtain an amount of blood adequate for the test.

The skin is consisted of two layers—the epidermis and the dermis. The capillary structures connected to the arterial and venous vascular beds rise vertically and are located in the dermis layer. The neural sensors such as Meissner's corpuscles and free nerve endings are also located in the dermis. Layers of subcutaneous tissues lie below the dermis. The supply arterial and venous capillaries are located laterally in this tissue bed. There is also adipose tissue interleaved with afferent and efferent nerve fibers along with their associated sensors interwoven within the vascular bed. To successfully obtain blood, a piercing device such as a needle or lancet must traverse the skin's various layers to reach the blood vasculature. The amount of force necessary to penetrate the skin surface will depend on the force applied normal to the surface of the skin needed to exceed the rupture strength. There exists an elastic range within which the degree of deflection corresponds directly with the applied force (skin depression). When the rupture limit is exceeded, a non-linear response by the skin (otherwise known as the inelastic response) occurs, corresponding to the further stretching of the skin at the point of application prior to rupture. Bleeding occurs when the penetration of the object reaches the capillary bed.

A few techniques can be applied to reduce the pain sensation in blood sampling. One way is by minimizing the lancing angle of penetration, and hence minimizing the building of pressure waves at the penetration site. In addition, optimizing the depth of penetration by the lancet or needle in the skin reduces the sensation of pain. Optimizing factors such as the above to reduce patient discomfort will encourage compliance in self testing, as an example, for diabetic self-monitoring.

A successful method to minimize pressure waves generated in the puncture of the skin by a needle, pin or lancet, etc., would be to minimize the area over which the puncture occurs. This can be achieved by miniaturizing the needle or lancet, provided the force applied to create the wound is minimal. The smaller the needle, the less force is required to puncture the skin, and less nerves endings are stimulated by the puncture. One method for reducing the needle diameter and still providing an adequate amount of blood for a desired analysis is to use multiple lancets, each having a smaller diameter than the minimum needle diameter needed for a single needle prick that would yield the same amount of blood. Lancet or needle devices with multiple lancets (or needles) for sampling blood are disclosed in commonly assigned, copending patent application "Multiple lancet device," invented by Lum et al., Attorney Docket No. 10980684-1, filed on the same day as the present application, which is herein incorporated by reference in its entirety.

Currently available lancet devices do not incorporate a combination of lancets and blood transporting structures. Blood measurement instrumentation currently available from vendors typically contains only blood transporting and measurement structures. This requires the user to set up several devices in order to produce a blood measurement on a sample of blood. Such devices include the lancet, lancet-launching device, blood collection structures, and the blood analyte measurement module or system. Juggling the use of so many devices can severely hamper the user's interest in compliance of monitoring his/her blood chemistry. What is needed is a comprehensive blood sampling system that is capable of eliciting the blood and transporting it immediately (i.e., without delay by storing it first) and directly to the measurement and sensing area. This system will incorporate the necessary structures and reagents for measurement, starting from the lancet, the blood transport structures, the measurement area, to the interface with the instrumentation. Furthermore, since some analyte assays are sensitive to dilution by interstitial fluid, the blood that initially emerges from a lancing wound ("initial blood") tends to contain more of such interstitial fluid than later portions. What is needed is a blood sampling device that is able to draw off and discard a first portion of the elicited blood and then deliver the remainder to the measurement area. In other words, what is needed is a device that can deliver a blood sample more representative of the circulating blood in the blood vessels.

Patents of interest about blood sampling devices are, for example, U.S. Pat. No. 3,358,689; U.S. Pat. No. 4,469,110; U.S. Pat. No. 4,627,445; U.S. Pat. No. 4,837,274; U.S. Pat. No. 4,995,402; U.S. Pat. No. 5,047,044; and U.S. Pat. No. 5,314,442.

SUMMARY OF THE INVENTION

The present invention is directed to a technique (including devices and methods) for sampling blood from a lancing wound on the skin of a patient. In one aspect, the present invention provides a device for sampling blood from the skin by lancet puncture. The device includes a unit having one or more fluid-conducting channels for conducting fluid from one or more openings that face against the skin being punctured. The device includes one or more lancets positioned near the unit to pass through the opening(s) on the unit to lance the skin when the lancet(s) are pressed towards the skin to result in the lancing wound. The unit can include a first channel for conducting away a portion (the first portion) of fluid that contains less of a fluid that is emitted from the lancing wound initially (initial fluid) and a second channel for conducting more of the initial fluid than the first channel. In blood sampling, when the skin is lanced, the initial fluid contains undesirable constituents such as interstitial fluid. In this way, the second channel can be used to carry a portion of fluid that has less of the undesirable constituents than the fluid in the first channel from the lancing wound to a measurement area.

The devices of the present invention have numerous advantages over prior blood sampling devices. First, with the incorporation of a fluid-conducting unit and a lancet, blood can be conveniently sampled and transferred to a desired location, such as a analytical site by simply placing the unit on the skin and pushing a button. In a preferred embodiment, through the use of two or more channels, one of which conducts away fluid that contains more of the initial fluid from the lancing wound, a blood sample that is more representative of the blood in the blood vessel can be delivered to an analysis instrument. Further, the lancing device having this capacity of selecting the proper blood portion can be made into a compact, convenient plate-shaped unit (hereinafter also called "plate unit"), which can easily be inserted into instruments that analyze and transmit the data electronically to distant locations. Also, multiple lancets can be arranged such that the distance between at least two of the lancets is within a limit such that the patient perceives only a single puncture when in fact more than one lancet puncture the skin.

Using the technique of the present invention, a person can conveniently sample blood and automatically ensure that the sample has little, if any, contamination by interstitial fluid. There is no need for the user to consciously take separate, deliberate steps to sample different portions. The convenience afforded by the present invention allows a multiple-step process to become a simple, one step, reproducible sampling and measurement process. As a result, a user will be more likely to closely comply with the self-monitoring program prescribed by health professionals.

DETAILED DESCRIPTION OF THE INVENTION

Figure 1:
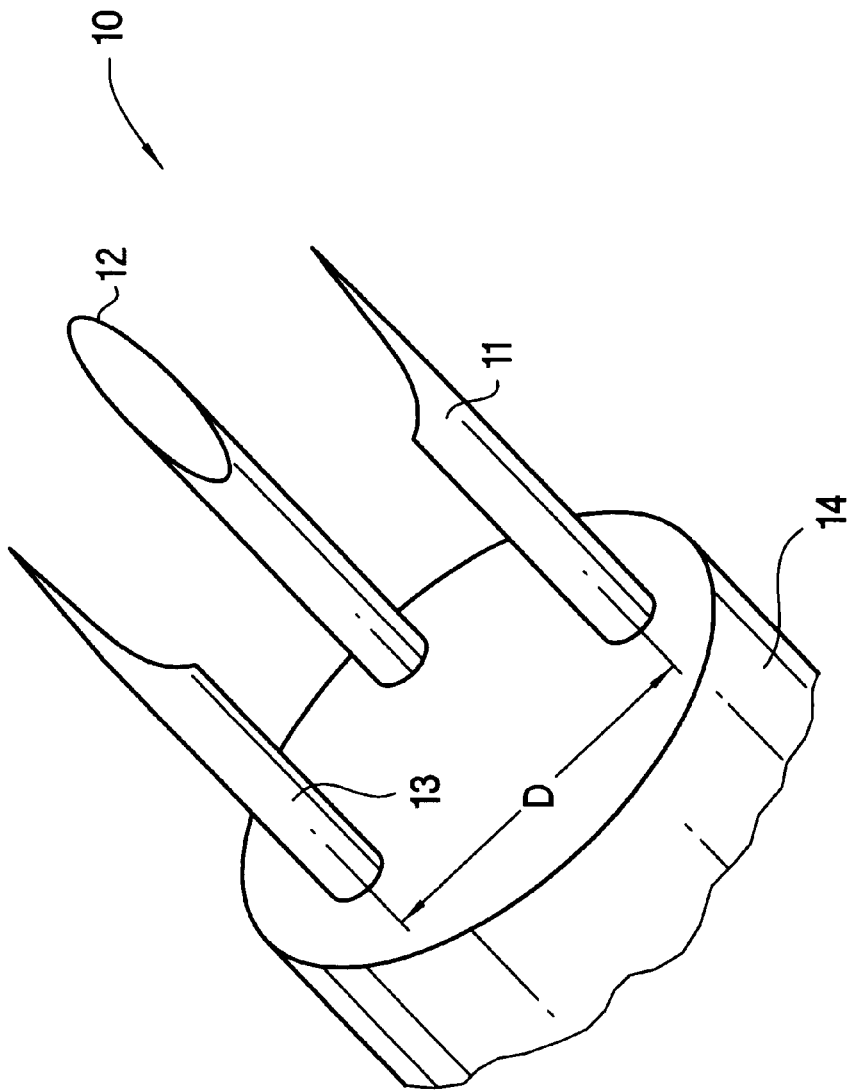
FIG. 1 is an embodiment of an isometric view of a multiple needle lancet device according to the present invention.

The present invention involves a technique to more conveniently obtain a more representative sample of blood from a patient. Since blood vessels are protected by a layer of living tissue that contains interstitial fluid, when the skin is punctured, the blood that first appears at the puncture site contains blood mixed with interstitial fluid, which does not have the same chemical or physical composition as the blood in the blood vessel. If the user is interested in knowing the properties of blood, for example, in monitoring certain blood electrolytes or other chemicals, a sample of blood with a minimal amount of interstitial fluid is required. Although, depending on the site of puncture and the physiological condition of the patient, the volume of the interstitial fluid emitting from a lancing wound may be relatively small compared with the volume of blood emitted, it is always more desirable to have less interstitial fluid in a sample for blood analysis. To this end, the present invention employs a technique of sampling blood by conducting a first portion away before a second portion of blood is conducted to the analysis instrumentation through a different channel. This disclosure further addresses a combination lancet device and blood extraction device for interfacing with current blood analysis equipment. As used herein, the term "lancet" refers to an elongated object with a sharp point for inserting into the skin to induce bleeding. Such a lancet may be needle-like with a round cross-section, or it may have cutting edge(s) along its elongated body for a cutting action to effect a less traumatic penetration into the skin. Also, the lancet can be hollow. When the term "lance," "puncture," "prick" or "penetrate" is used herein regarding a lancet, unless specified otherwise, it is to be understood that any of such lancets may be used.

Multiple Lancet Devices

Although a device with only one lancet can be used, in one preferred mode, the lancet apparatus of the present invention contains a lancet device having multiple lancets, such as those described in copending application, entitled "Multiple lancet device" (Attorney Docket Number 10980684-1), supra. Such a lancet device with multiple lancets works in conjunction with a series of tubes for rapid transport of a suitable portion to the measurement instrumentation and yet allows for the immediate disposal of a small quantity of blood that may contain undesirable materials such as interstitial fluid.

First, the lancet device having multiple lancets is briefly described in the following. The multiple lancets are positioned in the lancet device based on the observation that the ability of the human body to distinguish multiple punctures depends on the distance between the lancets. For any given location on a patient's body, there is a critical distance for distinguishing multiple puncture points. Puncturing by two lancets that are closer than this critical distance is perceived by the patient as a single puncture. The critical distance is different on various locations of the body. It is smallest on the fingers, being approximately 3 mm at the tips of the fingers. (See, e.g., Lawrence Krueger, *Pain and Touch*, page 3, Academic Press, San Diego, 1996). Accordingly, puncturing a finger tip by a multiple needle lancet device having needles that are less than 2 to 3 mm apart is perceived by the user as a puncture by a single needle. In the area of the finger tips, preferably, the distance between any two lancets is less than about 1.65 mm. This arrangement will provide an adequate space between lancets of, for example, 30 to 31 gauge (about 220 microns in diameter) needles. Since skin in other areas of the body is generally less sensitive than finger tips, often lancets can be arranged to be separated by more than about 3 mm between two individual lancets and still produce the sensation of only one puncture when the lancet device is applied to puncture the skin. By limiting the distance between lancets to under the critical distance of the particular area of the skin, the present invention provides lancet devices that draw sufficient blood and result in less pain than prior lancet devices.

FIG. 1 is a perspective view of an embodiment of a multiple needle lancet device 10 according to the present invention. For example, the lancet device 10 can include a tack-shaped structure having a head with multiple lancets. The lancet device 10 shown in FIG. 1 has three needles 11, 12, 13 whose tips are within a circle. Although needles are used in the lancet device 10, it is to be understood that any type of lancet with a long, slender body can be used. The distance, D, between any two of the needles 11–13 is chosen such that D is less than critical distance for the site on the patient's body at which the puncture is to be performed. In one preferred embodiment of the present invention, there are three needles that are spaced 1.65 mm from each other and are support by body 14. Thus, they are arranged in a triangular configuration.

Although in the above embodiment three needles are used, other numbers of needles and placement arrangements may be used provided the needles are arranged such that all of their lancet puncture wounds occur within an area whose boundary is limited such that the distance between any two needles is less than the critical distance. For example, an alternative embodiment includes 4 or more needles arranged as a ring, i.e., as the vertices of a polygon. It is preferred that the vertices sit on a circle that has a diameter equal or smaller than the critical distance for prick discrimination such that a prick by the device will be perceived as a prick from a single lancet. However, it is contemplated that the distance from one needle to one or more of the other needles can be larger than the critical distance, as long as the distance between two of the needles is less than the critical distance, thereby rendering these two needles indiscriminatable when the skin is lanced. Thus, when punctured by such a lancet tack, the user may perceive the lancet tack as containing more than one lancet but less than the actual total number of lancets, or even as only one lancet. It is also contemplated that the distance between various lancets need not be the same for all the lancets. However, generally, the total lancing foot print of the lancets of the lancet device on the skin preferably is less than about 4 mm, more preferably less than 3 mm, even more preferably less than 2 mm, from one side of a first lancet to the to the remote side of another lancet remote from the first lancet.

A preferred embodiment of the present invention includes a structure that stretches the skin for the puncture. For any given lancet, the condition of the skin has a significant effect on how it is punctured by the lancet. For example, if the skin is wrinkled, from the time the lancet touches the skin to the time it punctures it, the lancet may have traveled a considerable distance. This is because the lancet has to push the wrinkled skin until the skin is stretched taut enough to smooth out the wrinkles and exceed the puncture threshold before the lancet can penetrate. After the lancet has begun to penetrate the skin, due to the initial lack of tautness, the depth of lancet penetration into the skin cannot be controlled easily. In contrast, for skin that is taut, the lancet penetrates the skin a distance that is about the distance of the forward movement of the lancet. Therefore, it is easier to control the depth of lancet penetration when the skin is held taut prior to moving the lancet forward against the skin.

In the present invention, some embodiments can contain guiding openings (apertures), e.g., openings 105 shown in FIG. 2A (which will be described later), to control the sliding movement of the lancets. Further, a guiding aperture that is about the size of a lancet can be used to reduce pain. Details of such guiding apertures are fully described in copending application by Verdonk et al., Attorney Docket Number 10981587-1, entitled "Lancet device with skin movement control and ballistic preload," filed on even date as the present application and assigned to the same assignee as the present application, said copending application is incorporated by reference in its entirety herein. Briefly stated, as shown in FIG. 3, the bottom layer 126 of the lancet device has an aperture 134 that is about (i.e., slightly larger than) the size (i.e., the cross sectional size) of the lancet to guide the lancet 104, which can pass through the aperture 134 during the lancing movement. Preferably the area of the aperture 134 is less than twice the cross-sectional area of the lancet 104. The bottom layer 126 resting against the skin will restrict the vertical as well as the lateral movement of the skin that is in contact with it. When a lancet is about to puncture the skin, the initial contact of the lancet to the skin produces lateral, as well as vertical stretching of the skin as the lancet protrudes forward against the skin. Deformation of the skin and a propagating pressure wave results from this protrusion. This propagating pressure wave stimulates nerve endings and mechanoreceptors along its path. The stressing and straining of the skin tissue continues to increase until the elastic limit of the skin has been reached. At this instant, the sharp point of the lancet penetrates the skin tissue. For a needle-like lancet without cutting edges, upon reaching the elastic limit of the skin, tearing results due to the lack of a cutting edge. Often the shape of the wound resembled a three-pointed star.

Lancing with three-faceted lancets has demonstrated the same deformation in the skin prior to penetration. The wound is "C-shaped" due to the faceted cutting edges of the lancet. Lateral as well as vertical stretching of the skin surface still occurs. If the amount of unclamped, or exposed skin surface were to be restricted to approximately the diameter of the lancet, the lateral and vertical stretching of the skin is greatly restricted. This would result in a quicker breach of the skin with the lancet tip to create the required a skin incision. Reducing the area of lateral and vertical stretching would result in reducing the number of nerve endings and mechanoreceptors stimulated, and hence less pain perceived by the user during lancet penetration.

Figure 4:
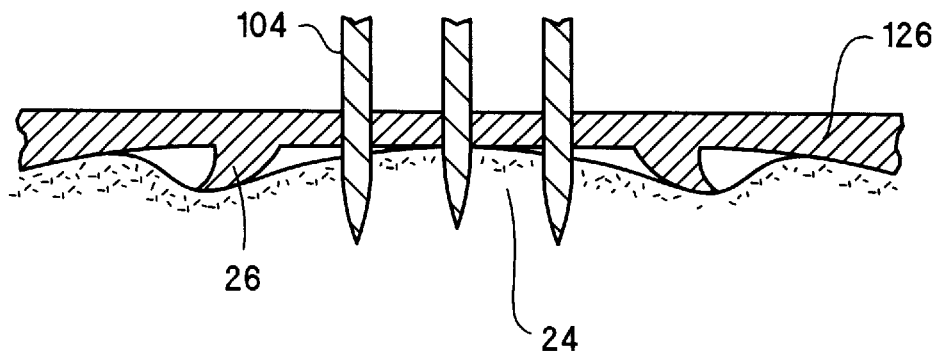
FIG. 4 shows a sectional view of a portion of an embodiment of a lancing apparatus of the present invention, having variable length multiple lancets
Figure 5:
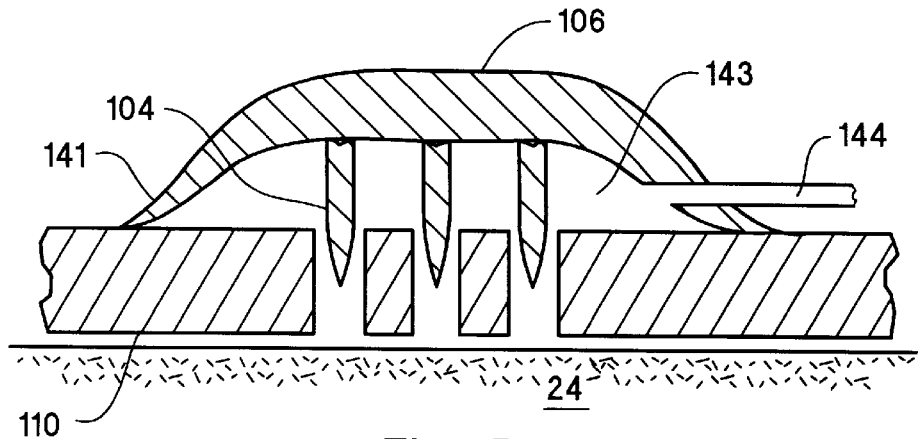
FIG. 5 shows a sectional view of a portion of an embodiment of a lancing apparatus of the present invention, having a resilient skirt supporting the lancets.

Furthermore, the lancets in the lancing device can be staggered in height to allow compensation of the curvature of the skin to obtain a uniform depth of penetration. FIG. 4 shows the lancets penetrating to the same depth in the skin, although they are at different distances from a bottom layer 126 of the lancing device. The curvature of the skin can either be due to the natural curvature of the part of the body at which the lancing takes place, or it can be due to compression by a flare 134 at the bottom of the bottom layer 126 of the lancing device on the skin. The needles are mounted to ensure a simultaneous penetration of the skin during a single moment in time. This would facilitate producing the sensory perception of a single needle penetration. Aforementioned copending application Docket Number 10980684-1 gives a more detailed description of lancet devices that have multiple lancets but whose lancing is perceived as caused by a single lancet. FIG. 5 shows an embodiment of a lancing device in portion, which has a resilient mechanism (or spring mechanism) that helps to pull the lancets 104 out of the skin 24 after lancing. The resilient mechanism has a ring-shaped lip 141 skirting the button top 106 and resting against a rigid part of the blood sampling device, such as plate unit 110 (which will be described below). The lip 141 is made of a resilient, deformable material such as a polymeric substance. The lip can be deformed when the button top 106 is pressed to permit the lancet to enter the skin. When the pressure is released from the button top 106, the memory of the lip 141 will resiliently push back on the top of the plate unit 110 to pull the lancet 104 from the skin. Furthermore, the lip 141, being ring-shaped, encircles the lancets 104 and forms a blood pooling chamber 143 and seals against leaks therefrom. As the spring action of the lip 141 pushes the button top 106 away from the skin, a suction is created inside the blood pooling chamber 143 to draw blood from the lancing wound. One or more channels 144 can be connected to the blood pooling chamber to draw blood away.

Multiple-channels for Conducting Blood

Figure 2A:
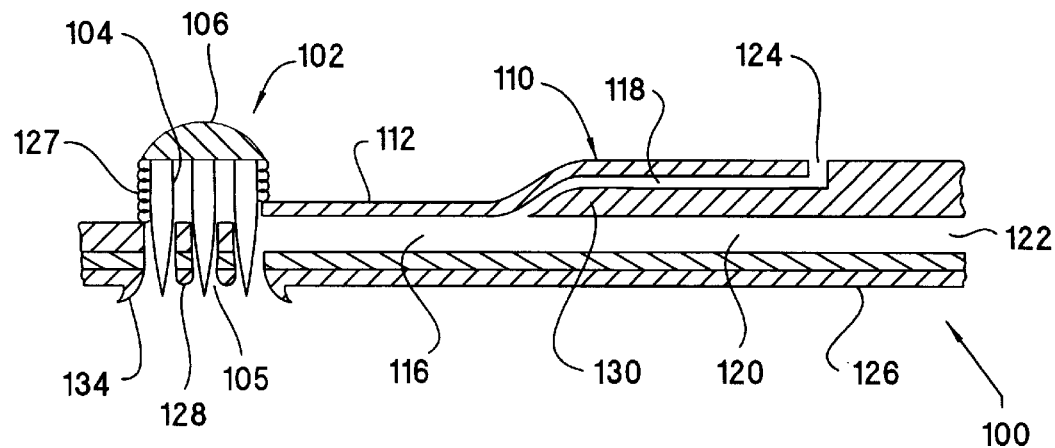
FIG. 2A shows a sectional view of a portion of an embodiment of a lancing apparatus of the present invention.
Figure 2B:
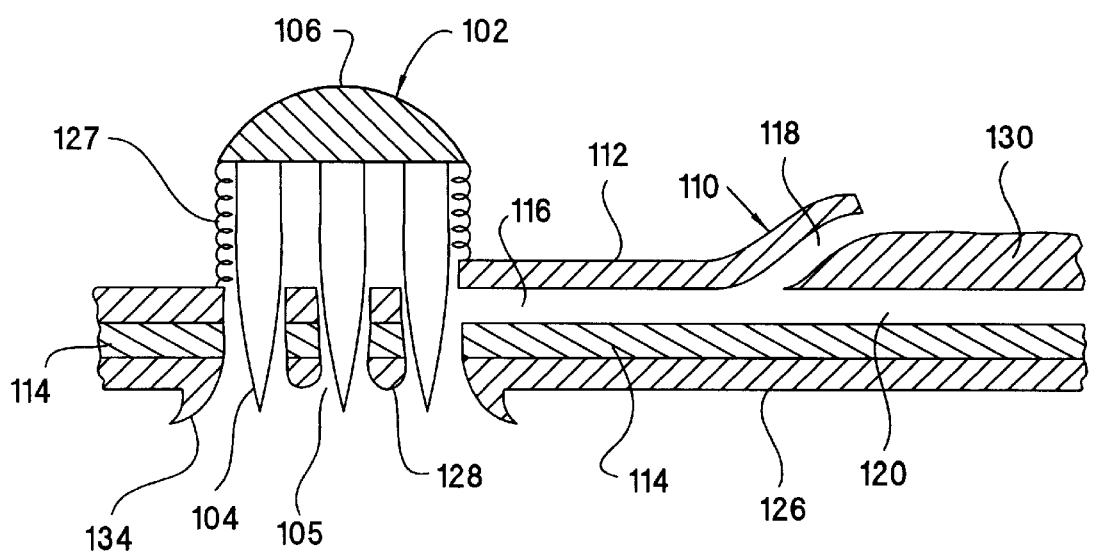
FIG. 2B shows further details of a portion of FIG. 2A.
Figure 2C:
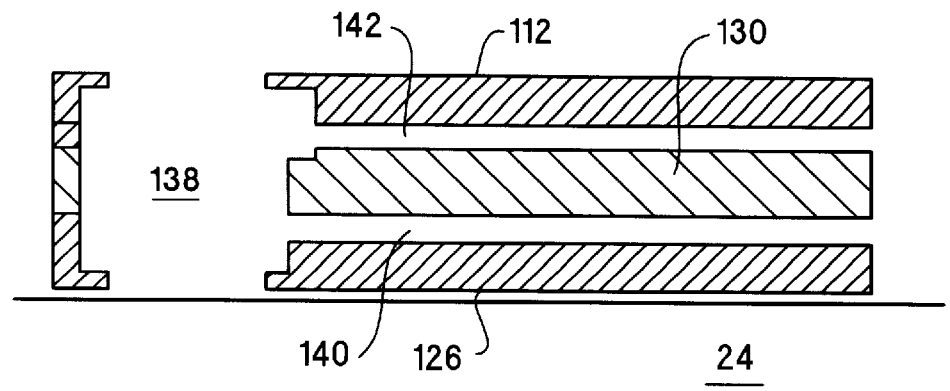
FIG. 2C shows a sectional view of a portion of another embodiment of a lancing apparatus of the present invention, having two channels.
Figure 3:
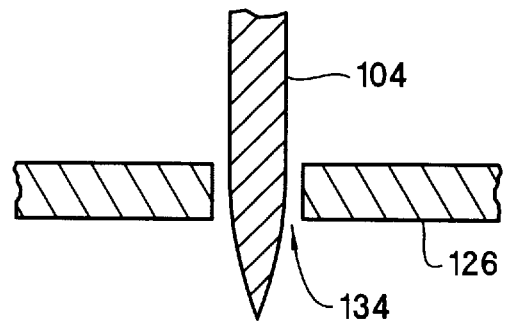
FIG. 3 shows a schematic sectional view of a guiding aperture for guiding a lancet.

One or more channels can be present in a device for conducting blood and other fluids according to the present invention, as shown in FIGS. 2A–2C. FIG. 2A shows a sectional view of a portion of an embodiment of a blood sampling device of the present invention. FIG. 2B shows a portion of FIG. 2A in more detail. The blood sampling device 100 includes a tack (or lancet applicator)102, which has three lancets 104 anchored to a head (or button top) 106. As used herein, although the term "tack" is used, it refers to a device with a head (i.e., top) with needle(s) (i.e., lancet(s)) thereon and does not necessarily direct to a device intended to be pressed into an object to remain in place. In fact, to sample blood, after the lancet punctures the tissue, normally it would be withdrawn to allow blood to emit from the puncture wound. The needles are preferably about 220 microns in diameter to provide adequate blood sampling capacity, and yet not occupy too much space to make D larger than the critical distance. A plate unit 110 having a relatively flat appearance has openings 105 through which the lancets 104 can pass. As used herein, the term "plate unit" when referring to a device having one or more channels describes a generally thin structure with two sides each having a relatively large surface area. It is not necessary that the two sides are completely flat, as long as the device has a generally flat appearance. The plate unit can have the appearance of a plate, slide, block, or a chip, as long as it has adequate space for the channels and an adequately flat surface for contacting the skin surface from which blood is being sampled. Plate unit 110 has a top layer 112 and an intermediate layer 114, between which is confined a capillary channel 116. The capillary channel 116 extends from the lancets and splits into two capillaries: a upper capillary 118 and a lower capillary 120 a distance from the lancets 104. The lower capillary ends at an opening 122 and the upper capillary ends at an exit port 124. Springs 127 are disposed between top layer 112 and the button top 106 for urging the button top 106 upward from the wound after lancing. The plate unit 110 optionally has a bottom layer 126, which provides a material of adequate coefficient of friction such that the device 100 can be held against the skin without slipping and sliding. Preferably, the layers 112, 114, 126 also provide guides 128 for guiding the lancets 104 as they move downward or upward. Further, the bottom layer 126 can have flaring lips (or skirt) 136 for exerting a radially outward (i.e. acting outward from the center of the area encircled by the lips) directing force on the skin to increase the tautness of the skin as the tack 102 is pressed against the skin.

The capillary channel 116 can be made by forming grooves on the top layer 112 and/or intermediate layer 114 and laminating the layers together. Similarly, the upper capillary 118 and lower capillary 120 can be formed by forming grooves on the top layer 112, intermediate layer 114, as well as on an interposing layer 130 between the top layer 112 and the intermediate layer 114.

Another embodiment having a two-level configuration of channels for sampling blood is shown in FIG. 2C. In this embodiment, elements for driving and controlling the movement of the lancet(s) and the device similar to those of FIG. 2A can be used, for example, button top 106, lancets 104, spring 127, guide 128, bottom layer 126, flaring lips 134, etc. However, for the sake of clarity in the figure, these are not shown in FIG. 2C. The blood sampling device has a blood collection chamber 138 defined by the top layer 112, intermediate layer 130 and bottom layer 126. The blood pooling chamber 138 is connected for fluid communication with a lower capillary 140 and an upper capillary 142. After lancing, blood coming from the lancing wound is allowed to collect in a blood pooling chamber 138. Thus, the blood that first exits from the wound will be drawn by capillary force into the lower capillary 140. After the lower capillary 140 is filled, the blood continues to rise in the blood pooling chamber 138. The blood that is emitted from the wound later will fill the upper capillary 142 and can be drawn for analysis.

Figure 6:
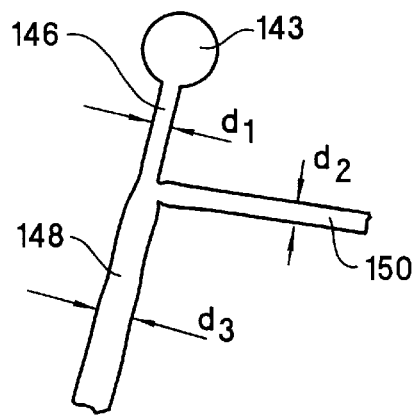
FIG. 6 shows a plan view showing channels for conducting fluid in an embodiment of a lancing apparatus of the present invention.
Figure 7:
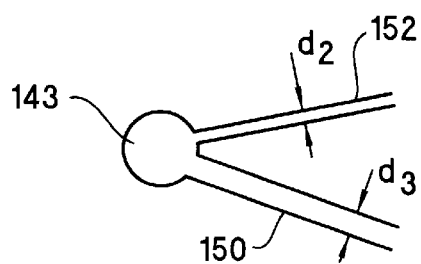
FIG. 7 shows a plan view showing channels for conducting fluid in another embodiment of a lancing apparatus of the present invention.

For drawing blood away from the lancing wound with capillaries, to not rely on gravity to dictate which capillary is filled first (as, for example, the devices of FIGS. 2A–2C do by the capillaries positioned at different elevations, i.e., having different vertical distances from the skin), the design of the blood routing can depend up the placement of two tubular capillaries within the blood pooling chamber 143. When two capillaries have openings at about the same place, if a first capillary is larger in diameter than a second capillary, a preferential flow path in the direction of the larger diameter capillary will result. This capillary fills with blood first. This is illustrated in FIG. 6, in which a blood pooling chamber 143 leads to a main channel 146 having diameter d1, which branches into larger secondary channel 148 having diameter d3 and a smaller secondary channel 150 having diameter d2. FIG. 7 shows an embodiment with a larger capillary 150 with diameter d3 and a smaller capillary 152 with diameter d2 are connected directly to the blood pooling chamber 143. In both of these embodiments liquid (such as blood) would initially enter both channels simultaneously by capillary force and the rate of flow of the larger diameter secondary channel is quicker than the smaller diameter secondary channel.

The following theoretical equations illustrate these facts. When a capillary has its entrance end in a liquid and is conducting the liquid such that the liquid forms a meniscus in the capillary, the pressure difference between the liquid surface at the meniscus and the liquid at the entrance of the capillary is $$\Delta P = (2\sigma \cos \theta)/r,$$

and the average velocity of the liquid flow in the capillary is $$V_{avg} = (\Delta P \, r^2)/(8 L_f \eta) = r\sigma \cos \theta/(4 L_f \eta)$$

Where:

$\Delta P$ is the pressure difference, $\sigma$ is the surface tension $\theta$ is the contact angle at the meniscus, $\eta$ is the viscosity $L_f$ is the length of the capillary to the liquid surface in the capillary, and r is the radius of the capillary.

These equations show that the velocity is proportional to the radius of the capillary.

Figure 8:
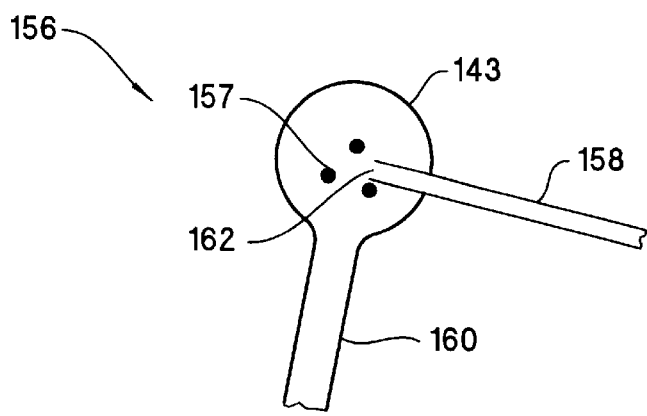
FIG. 8 shows a plan view showing channels for conducting fluid in yet another embodiment of a lancing apparatus of the present invention.

However, allowing blood to simultaneously enter both capillaries would result in the capillary used for channeling the blood to the measurement sensors receiving a certain amount of initial fluid from the lancing wound. Thus, preferably, one would want to separate the initial volume of blood from the subsequent volume of blood such that only the subsequent volume is contained in the second capillary, which leads to the measurement sensors. The embodiment of blood sampling device 156 shown in FIG. 8 has a first capillary 158 (which is smaller in this embodiment) in close proximity to the lancing wounds 157 such that it has quick access to a droplet of blood emerging from the wounds 157 in the blood pooling chamber 143, in order for the first capillary 158 to be filled first. A second capillary 160 (which is larger than the first capillary in this embodiment) is also connected to the blood pooling chamber 143, but with its entrance further away from the lancing wounds than the first capillary 158. Therefore the second capillary 160 in FIG. 8 will be filled only after the first, smaller capillary 158 has been filled.

Upon lancing, the blood initially pools in the blood pooling chamber 143. The first capillary 158, having an entrance opening 162 near to where blood is emerging from the skin, would come in contact with the first drop of blood and immediately begin to fill by capillary action. This initial volume of blood is usually discarded because of interstitial fluid contamination. When this first capillary 158 is filled, capillary action for the first capillary 158 ceases, and the blood pooling chamber 143 resumes to fill again. When the blood pooling chamber 143 fills and the blood comes in contact with the second capillary 160, capillary action begins to fill this tube. The result of the second capillary 160 is to transport a blood sample to biological sensors for analysis.

Figure 9A:
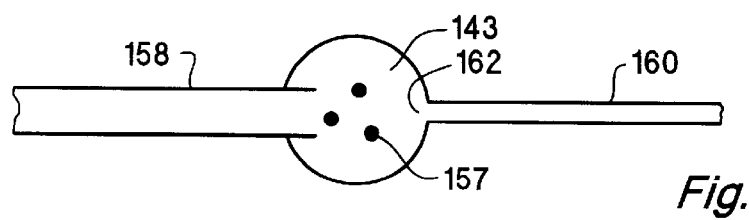
FIG. 9A shows a plan view showing channels for conducting fluid in yet another embodiment of a lancing apparatus of the present invention.

Whether the first capillary 158 closest to the wounds 157 should be larger or smaller than the second capillary 160 farther from the wounds 157 depends on how much of the first blood needs to be discarded. If more blood needs to be discarded, the first capillary 158 can be larger. This embodiment is shown in FIG. 9A. Further, the entrance 162 of the second capillary 160 can be a little removed from the center of the wounds to allow for a larger drop of blood to accumulate before blood is drawn into the second capillary 160. This would tend to reduce the risk of air entering the second capillary 160 to disrupt the capillary action. The size of the first capillary 158 for conducting the initial volume of blood is selected such that its capillary action draws blood away faster than the bleeding rate of the lancing wound. Generally, for a finger lancing wound, a capillary of larger than 500 microns internal diameter is adequate.

Figure 9B:
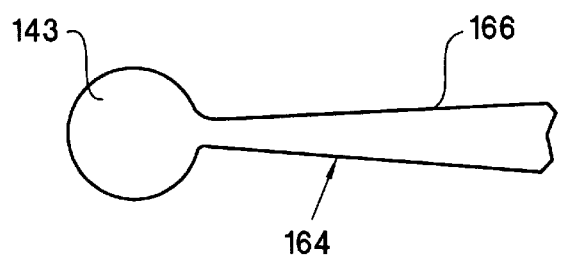
FIG. 9B shows a plan view showing a channel for conducting fluid with reduced risk of bubbles in yet another embodiment of a lancing apparatus of the present invention.
Figure 9C:
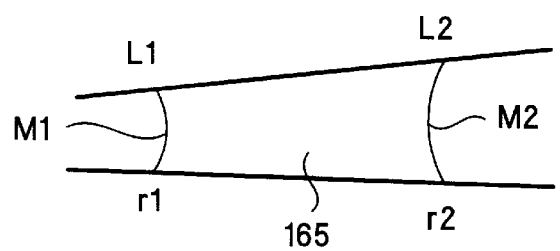
FIG. 9C shows a plan view illustration depicting pressure differences in a capillary at a flaring portion.

An alternative structure to reduce the risk of bubble formation in the capillary is shown in FIG. 9B, in which only one capillary is illustrated, although more capillaries can be used and have a similar feature for avoiding air bubbles. The capillary 164 has a flare portion 166 where it joins with the blood pooling chamber 143. Given this flare portion 166, which narrows the capillary down to a smaller diameter leading into the blood pooling chamber 143, when air is present at the entrance of the flare, the difference in surface tension at either end of the flare prevents a bubble from entering the capillary. The difference in surface tension will tend to drive the liquid towards the end of the smaller diameter. Bubbles are thus prevented from entering the flare from portion the blood pooling chamber 143. This is illustrated in FIG. 9C. In a flaring capillary, location L1 has a diameter of $r_1$ and location L2 has a diameter of $r_2$, the space between L1 and L2 is filled with a liquid 165. A meniscus M1 separate gas of pressure $P_A$ (e.g., atmospheric pressure) from the liquid at pressure at pressure $P_1$. A meniscus M2 separate gas of pressure $P_A$ from the liquid 165 at pressure $P_2$. If meniscus M1 at location L1 is absent (i.e., the entrance to the narrow end of the flare is filled with liquid) the liquid at L1 will be at the gas pressure $P_A$. Since $P_A$ is larger than $P_2$ of location L2 at which a meniscus M2 is present, liquid will flow from L1 to L2 when meniscus M2, but not meniscus M1, is present.

The pressure difference across M1 is $P_A - P_1 = (2\sigma \cos \theta) r_1$.
The pressure difference across M2 is $P_A - P_2 = (2\sigma \cos \theta) r_2$.
Therefore the pressure difference between L1 and L2, i.e., $P_2 - P_1$, in the liquid is $(2\sigma \cos \theta)/(1/r_1 - 1/r_2)$.

Since $r_2$ is larger than $r_1$, $P_2$ is larger than $P_1$. As a result, liquid flow from the wider end to the narrower end by capillary force.

Figure 10:
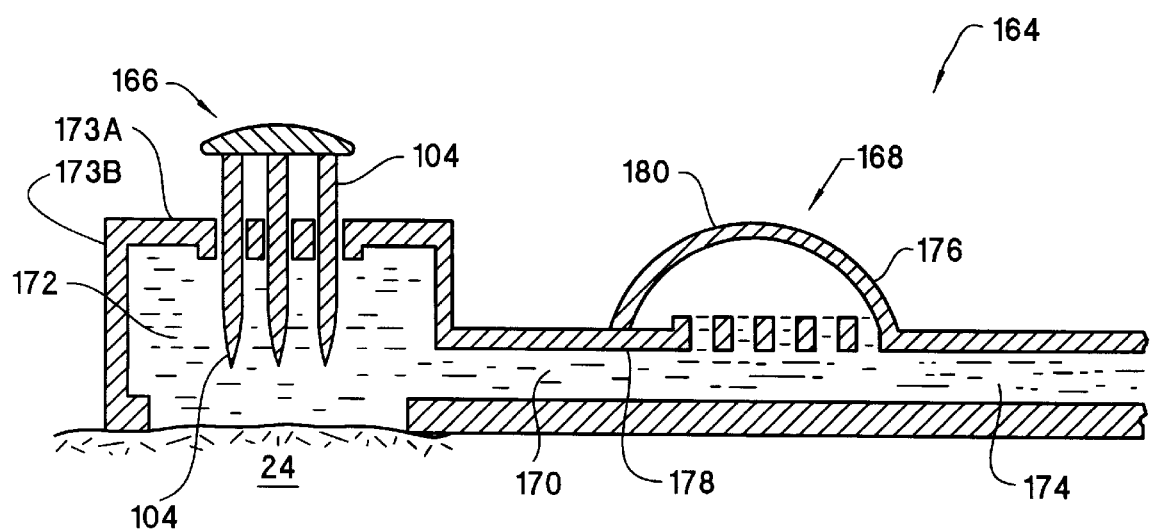
FIG. 10 shows a sectional view of an embodiment with an active transport mechanism.
Figure 11:
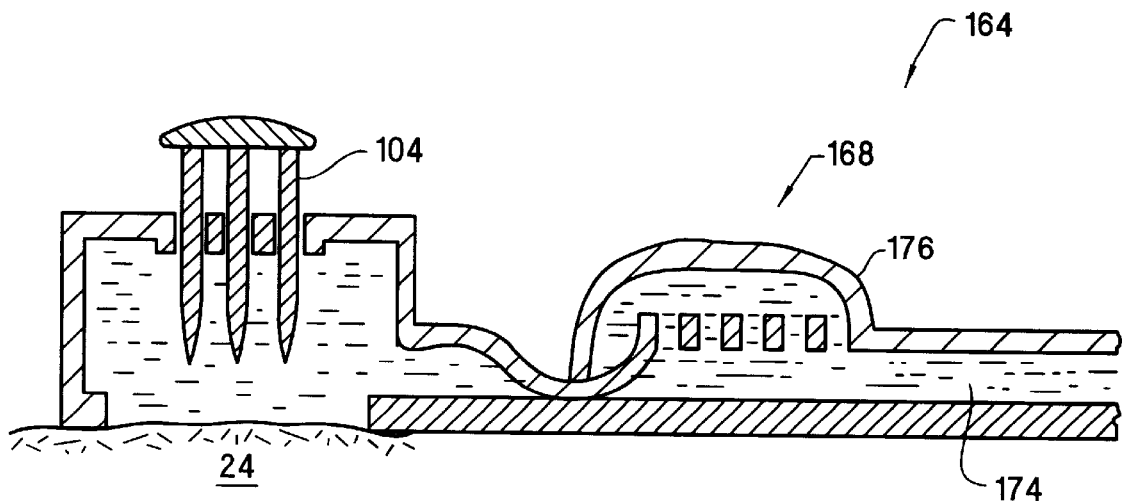
FIG. 11 shows a sectional view of the embodiment of FIG. 10 actively transporting blood in a channel.

A Pumping Mechanism Incorporated Into The Lancet Mechanism For Assisting Blood Extraction There are alternative techniques to using a multiple-capillary system for removing the initial blood. One technique in which the use of multiple capillaries is not needed is shown in FIG. 10, which includes an active transport mechanism. In FIG. 10, a chamber 172 having top wall 173A and side walls 173B is formed when device 164 is placed on the skin 24. The chamber 172 is connected via a channel 170 to access a pump 168, which assists to send blood to a desired location. The blood sampling device 164 includes a tack 166 that has lancets 104 that protrude into the chamber 172. The tack 166 is similar to above-described embodiments such as those of FIG. 2A and FIG. 5 (other features such as springs for removing the lancets from the skin after lancing are not shown in FIG. 10 for clarity). By pressing the tack 166 to drive the lancets 104 through the chamber 172 the skin 24 can be lanced. After the lancets are withdrawn from the skin, blood is emitted from the wound in the skin 24 and fills the chamber 172. Blood also passes from the channel 170 to be acted on by the pump 168. By the assistance of the pump 168 blood is sent to the channel 174 to flow downstream. The pump 168 includes a collapsible bubble 176. A portion of the channel 170 has a collapsible wall 178. When the collapsible bubble 176 is pressed, the downward force presses on the collapsible wall 178 and closes that portion of the channel 170. See FIG. 11. The structure and material of construction of the collapsible bubble 176 are selected such that there is no significant change in volume inside the bubble as the force applied to the bubble is increased until a limit is reached. Once the limit is reached, the top 180 of the collapsible bubble 176 collapses and the volume inside the collapsible bubble suddenly decreases significantly due to the top's 180 collapse. As a result of this decrease in volume in the collapsible bubble 176 and because the channel 170 is blocked, blood in the channel 174 is forced (i.e., pumped, actively transported) to travel in the direction away from the tack 166.

Use of Suction to Assist Blood Sampling

Figure 12:
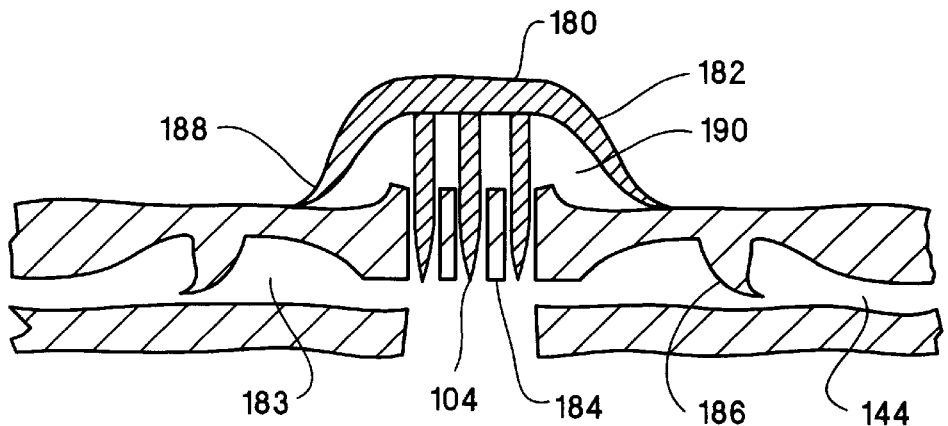
FIG. 12 shows a sectional view of an embodiment with a suction-assist mechanism.

Suction-assisted blood extraction might also be incorporated into the afore-mentioned planar tubular system. One method is to incorporate a suction source into the lancet support structure shown in FIG. 12. This technique is different from that of suction-assisted perfusion of the skin surface prior to lancet application. The present technique creates a suction at the moment of lancet withdrawal from the wound. The suction helps to draw blood from the wound site. FIG. 12 illustrates a structure that incorporates lancet support 184 that guides the lancets as the lancets are driven toward or away from the skin. The lancets are attached to the top 180 of a suction-generating chamber bubble 182. The channel 183 through which blood can be passed from the wound has check valves 186 for maintaining a suction in the chamber 190. The channel 183 can be split into two or more channels similar to those in FIG. 2A to remove the initial blood as well as to deliver a representative blood sample to be analyzed.

Figure 13:
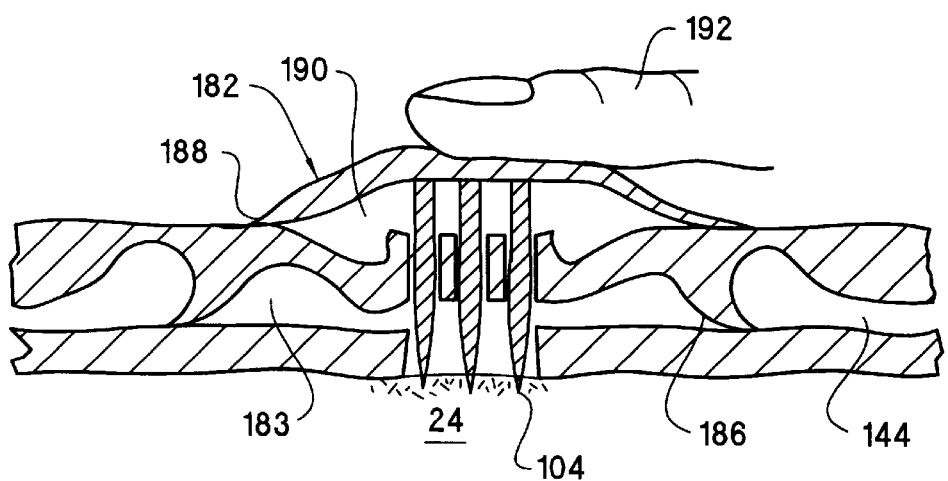
FIG. 13 shows a sectional view of the embodiment with a suction-assist mechanism of FIG. 12 under full deformation when under pressure.
Figure 14:
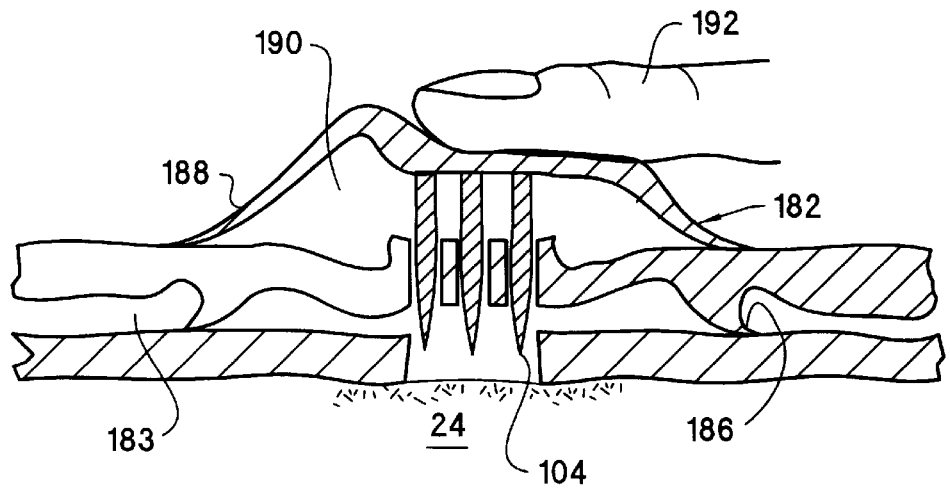
FIG. 14 shows a sectional view of the embodiment with a suction-assist mechanism of FIG. 12 under partial deformation.

The sequence of events for a typical suction-assist method is as follows (see FIG. 13): A user (e.g., by using finger 192) would press the lancet chamber bubble 182 and force the lancet(s) 104 to penetrate the skin 24. As the chamber bubble 182 is collapsing under pressure, air is purged from the chamber 180 through the check valve 186 toward the distal end of channel 144. Also, the skirt 188 (i.e., the chamber walls) due to its design, adjacent to the capillary tubes would collapse. This initial collapse would create a suction-seal for the chamber 190 and prevent fluid leakage into the capillary tube structure from outside the chamber bubble 182. The chamber bubble 182 continues to collapse until the lancets 104 reach their designed maximum penetration depth into the skin 24. The material of construction and the dimensions of the feature are selected such that when the user releases the pressure from the chamber bubble 182, the chamber 190 would return to its original shape before the check valves 186 open again, as shown in FIG. 14. This "memory" redeployment of the chamber bubble 182 creates the necessary suction for assisting in the additional extraction of blood from the skin 24. The check valves 186 thus facilitate a pumping action that moves blood away from the lancing site.

Figure 15:
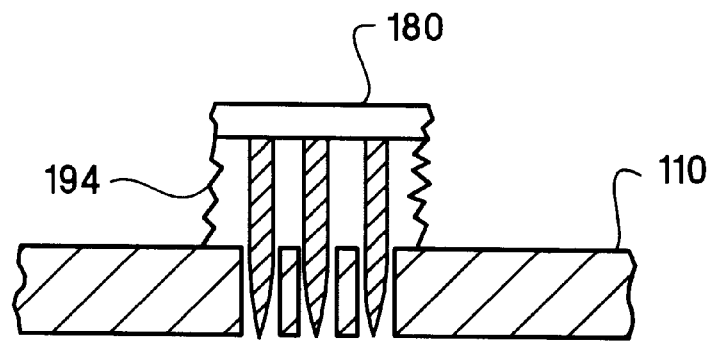
FIG. 15 shows a sectional view of an alternate embodiment of a suction-assist mechanism.

Another embodiment for creating a suction for assisting blood to flow from the lancet wound into the sampling device is by the use of a bellow mechanism. The bellow takes the place of the collapsible bubble in the previous embodiment. The structure shown in FIG. 15 is similar to that of FIG. 12 except it has a bellow 194. For clarity of description not all details of the device are shown. The top side of the bellow 194 is connected to a top 180 on which the lancets 104 are attached. The bottom side of the bellow is connected to the plate unit 110.

Figure 16:
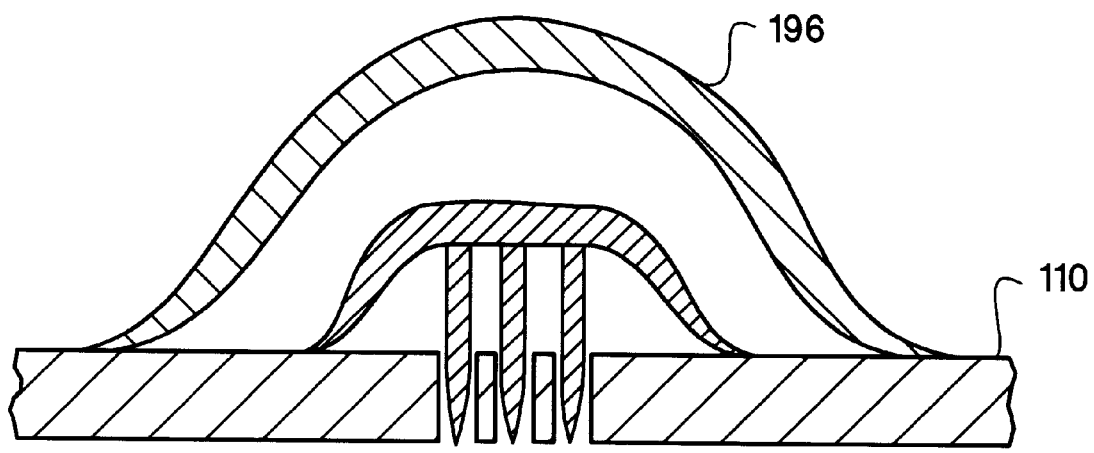
FIG. 16 shows a sectional view of an alternate embodiment of suction-assist mechanism with double buttons.

A double bubble structure, as shown in FIG. 16, can also be used. The larger outer bubble 196 generates the suction while the smaller inner bubble 192 controls the lancets' 104 movement on the plate unit 110. A check valve mechanism similar to that described earlier can be applicable in this device as well to improve the suction during blood extraction. Again, for clarity of description, not all details of the device are shown.

Control of Fluid Movement About the Blood Pooling Chamber

Figure 17:
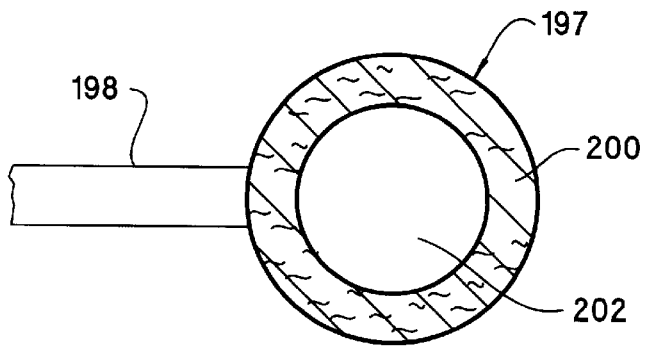
FIG. 17 shows a schematic view of an embodiment employing an absorbent material.
Figure 18:
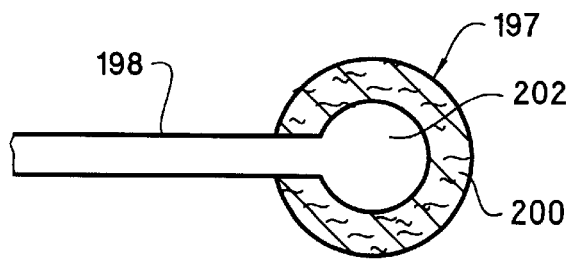
FIG. 18 shows a schematic view of an alternate embodiment employing an absorbent material.

An absorbent material such as a sponge, fibrous material, material with capillaries, and the like, can be used for encircling the blood pool chamber for retaining the initial blood before blood is conducted to a measurement sensor. FIG. 17 shows schematically such an embodiment. In the peripheral portion of the blood pooling chamber 197 is placed an absorbent material. As shown in FIG. 17, the placement of the capillary tube (i.e., channel) 198 for transporting the blood away from the lancet wound may be placed behind the absorbent material 200 such that the absorbent material 200 interposes between the capillary tube 198 and the wound. Blood must pass through the absorbent material 200 before reaching the capillary tube 198, as shown in FIG. 17. The blood is absorbed preferably into the absorbent material 200 due to capillary action. Once the blood has completely saturated the absorbent material 200, the rest of the blood pooling chamber 197 fills. In an alternative embodiment, the capillary tube 198 protrudes past the absorbent material 200 into the more central portion 202 of the blood pooling chamber 197, as shown in FIG. 18. This configuration tends to minimize the effects of contamination of the blood passing through the capillary 198 by the initial blood.

Figure 19:
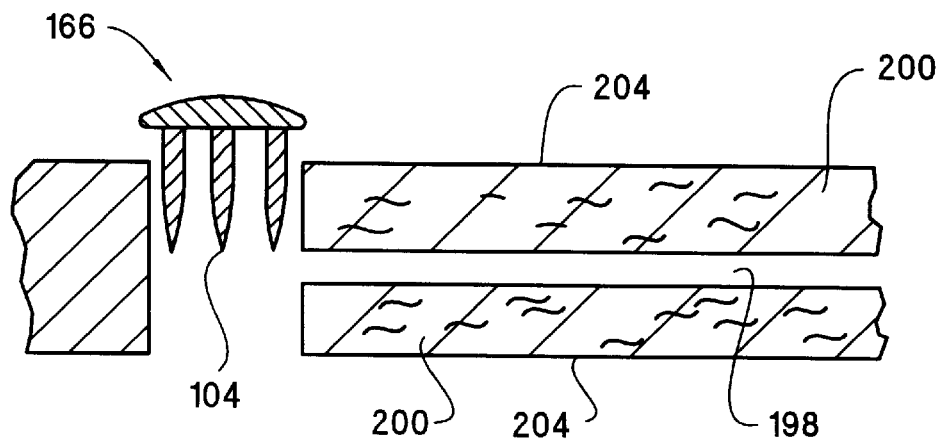
FIG. 19 shows a schematic view of another alternative embodiment using an absorbent material.

Yet another technique to remove initial blood during sampling to reduce contamination by interstitial fluid is to append a reservoir 204 (shown in FIG. 19 as containing an absorbent material 200) about the beginning portion of the capillary tube 198. After lancing, the initial blood is captured in the reservoir 204. Blood for analysis is contained in the structure including the capillary tube 198. One way to transfer the blood for measurement analysis is to remove the capillary tube 198 from the tack 166 and dispense the blood therein for dispensing into a receptacle of the measurement system. The blood contained in the reservoir 204 is not dispensed. However, there may still be some contamination by initial blood in the channel 198 with this technique due to the common flow path in the capillary tube 198.

The design with absorbent material or reservoir can further incorporate an active transport mechanism for pumping the blood fluid is shown in FIG. 10. As in the embodiment of FIG. 10 a second bubble for pumping is needed, as is the check valve mechanism.

Incorporation Of A Lancet Device On A Planar Blood Sampling System

Many of the commercially available lancet devices are spring driven and the driving mechanism cost is far more than the lancet itself. The use of such a device requires the user to load a disposable lancet into the lancet device. The size of the lancet device would exceed that of the lancet and the blood measurement sensor unit. The basic advantage of such lancet devices is their ability to launch a lancet into and withdraw it out of the finger very quickly. One method to provide the quick striking and withdrawal action in the lancet device on a planar structure that contains the aforementioned blood disposal and sampling structures would be the incorporation of binary memory materials to assist the user in reducing the time of lancet penetration and dwelling in the finger. This can replace the spring driven lancet device. Binary materials are known in the art (see, e.g., U.S. Pat. No. 4,857,274 and U.S. Pat. No. 4,301,412).

Figure 20:
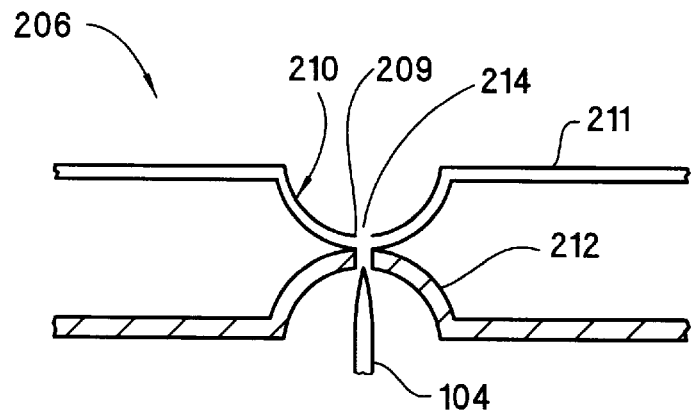
FIG. 20 to FIG. 24 show sectional views of an embodiment using a binary deformation material to control lancet movement.
Figure 21:
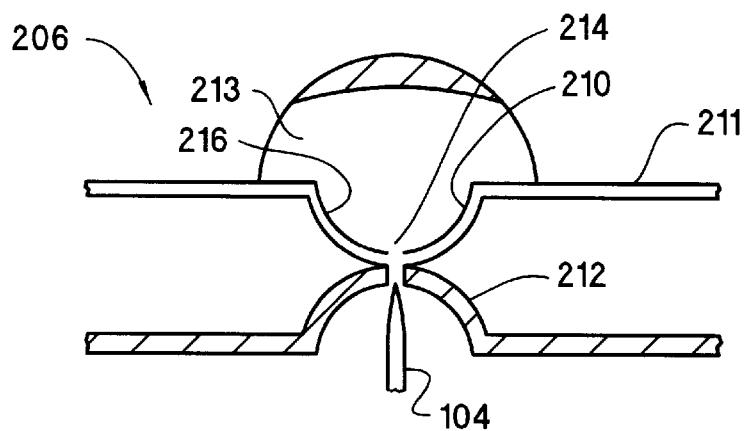
Figure 22:
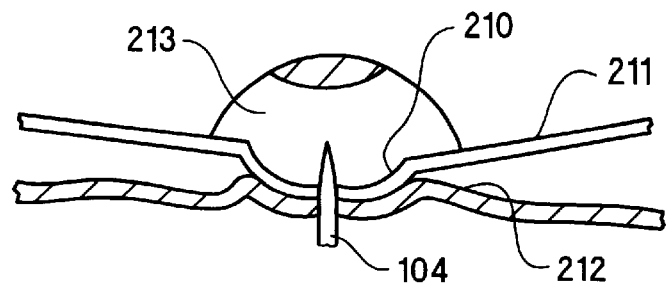
Figure 23:
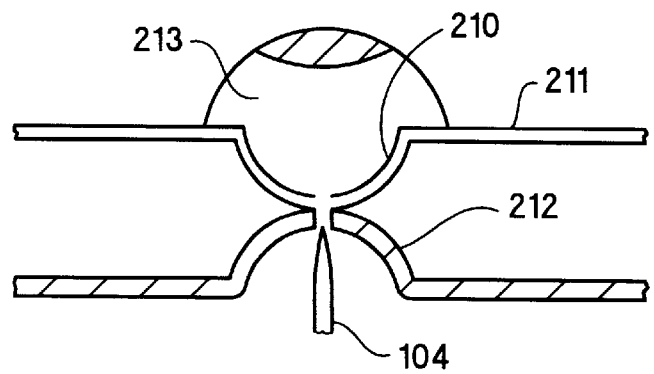
Figure 24:
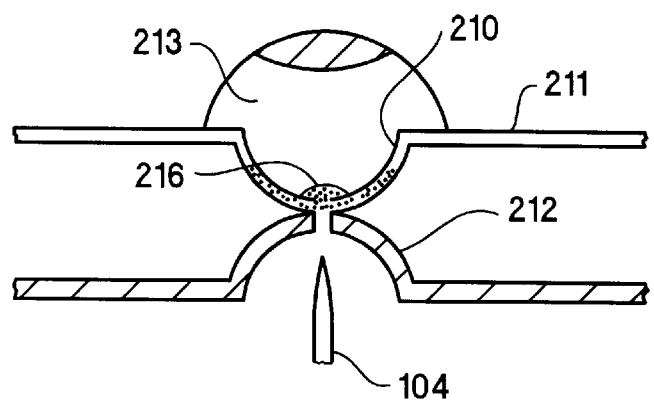

A device containing a binary material for driving and withdrawing lancet(s) is illustrated in FIG. 20. The device contains a planar unit 206 similar to the plate unit 110 of FIG. 2A, which contains channels for disposal and sampling of blood. On the planar unit 206 is a half spherical indentation 210 large enough to accommodate a finger or a small section of the glabrous portion of the forearm. The indentation 210 contains the entry ports 209 for the capillary tubes 211 for either initial blood discard or transport to the measurement sensor system. Beneath the indentation 210 there is a bubble structure 212 made of binary material, preferably plastic for ease of construction, shielding the user from a lancet 104 (or a group of lancets). When the user places a finger 213 upon the indentation 210 on the planar surface, a small guidance aperture 214 in the indentation surface 216 would help limit the skin deformation, similar to the way an aperture reduces skin deformation described supra. The aperture 214 is around the location for lancet penetration. The user gradually presses down upon the surface 216 over the indentation 210 with the finger as shown in FIG. 21. The plastic binary bubble structure 212 has been designed to resist pressure but to yield quickly when a particular pressure is reached. Upon exceeding this yield limit the bubble structure 212 immediately collapses allowing the lancet 104 to protrude into the finger 213. The lancet penetration depth into the finger 213 is physically limited by the structure as in FIG. 22. Upon the sensation of the lancet penetrating the skin, the user would partially release some of the finger pressure on the indentation 210 area. This lessening of pressure against the binary material bubble 212 would cause the binary material to return the bubble 212 to its former shape. The memory in the plastic material would return the binary material bubble structure to its original shape resulting in a quick repulsion of the finger 213 from the lancet 104 as shown in FIG. 23. The finger 213 would begin to bleed immediately and the blood 216 pool would be collected in the half spherical indentation and conducted away by the capillary 211 for disposal and sampling, as is shown FIG. 24.

This launching device demonstrates a method of incorporating a low cost lancet device onto a planar blood sampling structure. The device allows for a rapid entry and extraction of the lancet from the user's finger, which minimizes pain.

Incorporation Of A Lancet Device On An Analysis System

Figure 25:
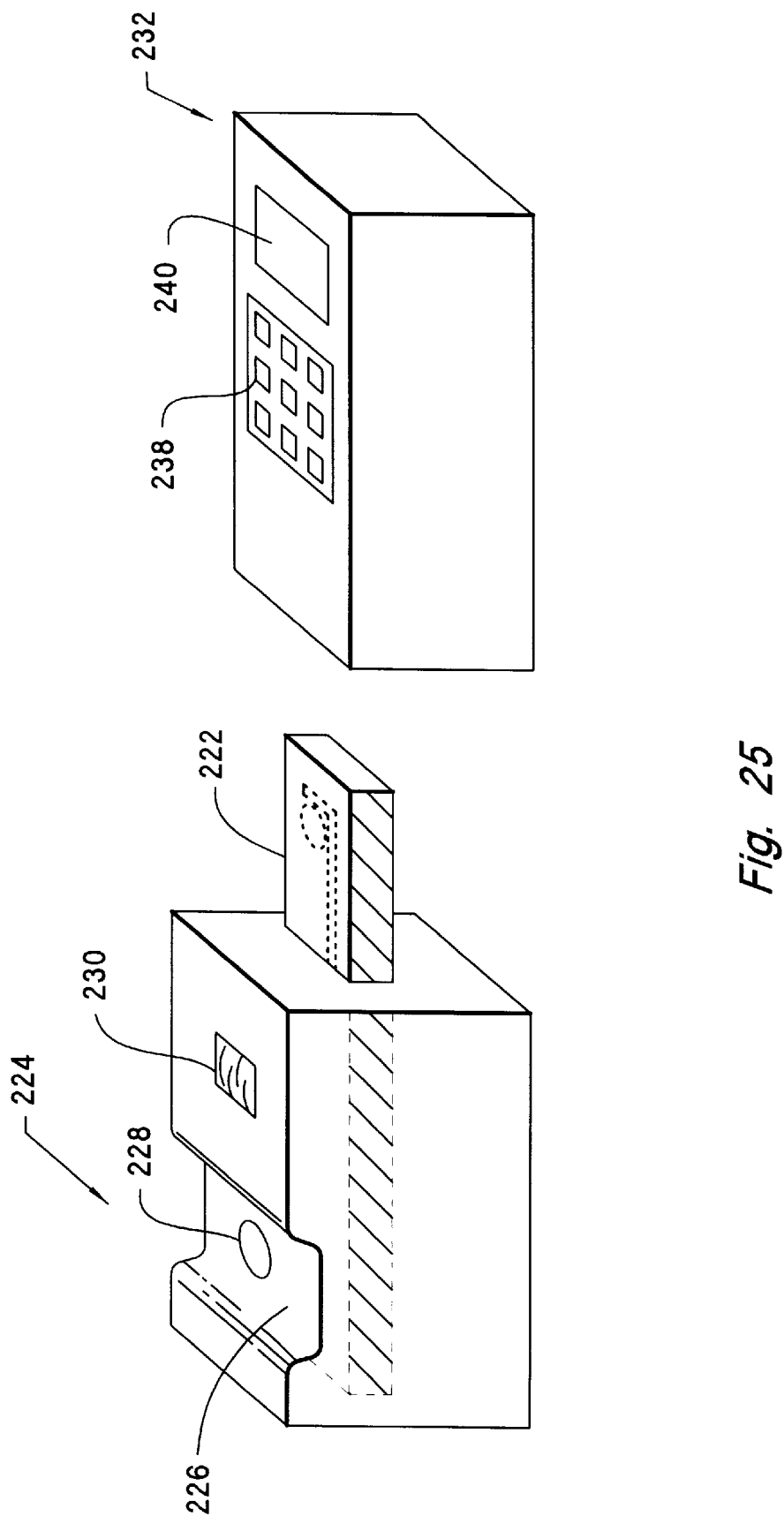
FIG. 25 shows an isometric view of an embodiment of a system for lancing and analyzing blood from lancing.

The planar blood sampling devices of the present invention, for example, those aforemention embodiments, can be incorporated into a system, including chemistry and electronics, for analysis, computation, and data communication. FIG. 25 shows such a system. Chemical and optical techniques for analysis, as well as the electronics and computer hardware and software for data transmission and data analysis are known in the art and will not be described herein. Basically, in this system 220 the planar blood sampling device 222, similar to those described in the above, can be inserted in to a lancing unit 224. The lancing unit 224 can have a slot 226 on which a part of the user's skin, such as that of a finger, can be pressed for lancing. In the slot 226 is an opening 228 through which the skin can be exposed for lancing by the lancet 104 (not shown in the figure). The lancet in the planar blood sampling device 222 can be pressed to extend into the opening 228 to lance the skin. The lancing unit can have a mechanism, such as one containing levers, pivots, and springs, that can be activated by a button 230 to drive the lancet. This mechanism can, for example, push on the button top 106 of a planar blood sampling device of FIG. 2A. The opening 228 can be big enough and the planar blood sampling device 222 can be near to the opening 228 that a planar blood sampling device of FIG. 20 can be used. The planar blood sampling device 222 can have one end extending out of the lancing unit 224 for inserting into a communication unit 232. The communication unit 232 has data analysis capacity. It can also contain the chemical and optical analysis mechanisms. Optionally, the chemical analysis can be performed in the planar blood sampling device 222 if proper chemical agents are included in it. A typical analysis is the glucose content of the blood. Input devices such as keys 238 for introducing control or programming parameters into the communication unit 232 can be present thereon. Further the communication unit 232 can have a display 240 for displaying information, such as the parameter being keyed in, the result of analysis, and the like, to a user. Methods for the lancing, sampling and analysis of blood for glucose are well known in the art. Further integrated systems for lancing and analysis are also disclosed in commonly assigned, copending application, Attorney Docket No. 10970322-1, entitled, "Integrated system and method for sampling blood and analysis," which is incorporated by reference in its entirety herein.

Although the above-described embodiments of the present invention have been described in terms of lancets using "needles" as a preferred embodiment, other forms of puncture devices may be utilized. For example, the puncture devices could be in the form of small oblong blades. Various modifications to the present invention will become apparent to those skilled in the art from the foregoing description and accompanying drawings. Furthermore, it is to be understood that the present invention may be applied in nonmedical technologies. For example, when a certain object, e.g., a plant, a container, etc., emits a fluid that might change composition with time after the outer surface or layer is damaged or opened, a device having multiple channels as in the present invention can be used to sample the fluid emitted from the object. Further, lancet devices may be used on other animals, including reptiles, domestic mammals, and the like. Although the scientific theory relating to the present invention has been described in detail, the application of the present invention is not dependent on any particular theory. A person skilled in the art will be able to practice the invention based on the present disclosure.

What is claimed is:

1. A device for sampling blood from the skin of a patient, the device comprising:

(a) fluid-conducting plate unit having one or more openings for facing against the skin of a patient, through which openings one or more lancets can pass to puncture the skin to result in a puncture wound, the plate unit having channels each for conducting fluid from the puncture wound; and (b) one or more lancets positioned near the plate unit associated therewith for passing through the one or more openings to puncture the skin when pressed into the skin;

wherein the plate unit comprises a first channel for conducting away a first portion of the fluid and a second channel for conducting a second portion of the fluid.

2. A device according to claim 1, wherein the first channel and the second have channel one or both of a difference in size and a difference in position relative to the bleeding wounds such that the first channel conducts a fluid that contains more of a fluid that is emitted initially (initial fluid) from the puncture wound and a second channel conducts a second portion of fluid that contains less of the initial fluid.

3. A device according to claim 1, wherein the plate unit further comprises a chamber into which liquid can enter from the one or more openings on the plate unit, the first channel and the second channel being in fluid communication with the chamber.

4. A device according to claim 1, wherein each channel has an entrance portion each having an average diameter, the entrance portion of the second channel having an average diameter larger than the average diameter of the entrance portion of the first channel such that capillary force draws fluid at a faster volume flow rate into the first channel than in the second channel.

5. A device according to claim 1, wherein the plate unit further comprises a chamber into which blood can enter from the one or more openings on the plate unit, the first channel and the second channel being connected for fluid communication with the chamber.

6. A device according to claim 1, wherein the second channel has a one way valve and a pump to pump fluid away from the puncture wound.

7. A device according to claim 1, wherein the first channel is a passageway in a sponge structure.

8. A device according to claim 1, wherein the first channel is a passageway in a sponge structure, wherein the sponge structure is connected towards the end portion of the second channel such that the initial fluid that passes through the second channel will be soaked up by the sponge structure, and wherein the second channel has a distal end opening for analysis of liquid sample conducted through the second channel.

9. A device according to claim 1, further comprising a detector at the end of the second channel for detecting property of blood conducted through the second channel.

10. A device according to claim 1, further comprising a detector at the end of the second channel for detecting property of the fluid conducted through the second channel, the detector including electronics and a display for processing data of the detected property, the device being of a hand-held size.

11. A device for sampling blood from the skin of a patient, the device comprising:
(a) fluid-conducting plate unit having one or more openings for facing against the skin of a patient, through which openings one or more lancets can pass to puncture the skin to result in a puncture wound, the plate unit having multiple channels each for conducting fluid from the puncture wound; and
(b) one or more lancets positioned near the plate unit associated therewith for passing through the one or more openings to puncture the skin when pressed into the skin;
wherein the plate unit's openings against the skin are surrounded by a resilient flexible lip that applies a radially outward force to the skin when the lip is pressed against the skin.

12. A device according to claim 11, wherein the lip comprises a polymeric material enabling the lip to deform when it is pressed against the skin.

13. A device for sampling blood from the skin of a patient, the device comprising:

(a) fluid-conducting plate unit having one or more openings for facing against the skin of a patient, through which openings one or more lancets can pass to puncture the skin to result in a puncture wound, the plate unit having multiple channels each for conducting fluid from the puncture wound; and
(b) a plurality of lancets positioned near the plate unit associated therewith for passing through the one or more openings to puncture the skin when pressed into the skin;
wherein each of the lancets is at less than a distance DD from another of the lancets, the distance DD being chosen to be about the discriminatable distance between distinct pain perception points in the patient, such that the patient would perceive a single puncture when two lancets at less than distance DD apart puncture the skin.

14. A device for sampling blood from the skin of a patient, the device comprising:
(a) fluid-conducting plate unit having one or more openings for facing against the skin of a patient, through which openings one or more lancets can pass to puncture the skin to result in a puncture wound, the plate unit having one of more channels each for conducting fluid from the puncture wound; and
(b) one or more lancets positioned near the plate unit associated therewith for passing through the one or more openings to puncture the skin when pressed into the skin;
the device additionally comprising a plurality of lancets and wherein the plate unit has a plurality of openings each for allowing a lancet to pass through to puncture the skin.

15. A device according to claim 14, wherein the openings are each about the size of a lancet to allow the lancet to pass through.

16. A device for sampling blood from the skin of a patient, the device comprising:
(a) fluid-conducting plate unit having one or more openings for facing against the skin of a patient, through which openings one or more lancets can pass to puncture the skin to result in a puncture wound, the plate unit having multiple channels each for conducting fluid from the puncture wound; and
(b) a plurality of lancets positioned near the plate unit associated therewith for passing through the one or more openings to puncture the skin when pressed into the skin;
the device further comprising a top from which the one or more lancets are anchored such that pressing the top causes the one or more lancets to press against the skin.

17. A device according to claim 16, wherein the top has a resilient member contacting the plate unit, the resilient member is compressed when the top is pressed to drive the one or more lancets into the skin and springs back to its original shape to pull the lancets from the skin after the pressure on the top is released.

18. A device for sampling blood from the skin of a patient, the device comprising:
(a) fluid-conducting plate unit having one or more openings for facing against the skin of a patient, through which openings one or more lancets can pass to puncture the skin to result in a puncture wound, the plate unit having one or more channels each for conducting fluid from the puncture wound; and (b) a plurality of lancets positioned near the plate unit associated therewith for passing through the one or more opening to puncture the skin when pressed into the skin;

wherein at least one of the one or more channels has a flaring portion to inhibit a bubble from entering into the channel.

19. A device for puncturing the skin of a patient to sample blood, comprising:

(a) fluid-conducting plate unit having one or more openings for facing against the skin being punctured, the plate unit having a first channel for conducting away a first portion of fluid that contains more of a fluid that is emitted initially (initial fluid) from the skin after puncture and a second channel for conducting a second portion of fluid containing less of the initial fluid; and (b) a plurality of lancets positioned near the plate unit, the lancets each passing through one of the one or more openings on the plate unit and puncturing the skin when pressed against the skin to yield blood.

20. A device according to claim 19, further comprising a housing associated with the plate unit for housing the plate unit and the lancets, the housing having a detector for detecting a property of the second portion of fluid.

21. A device for puncturing the skin of a patient to sample blood, comprising:

(a) fluid-conducting plate unit having one or more openings for facing against the skin being punctured, through which openings a plurality of lancets can pass to puncture the skin to yield blood, the plate unit having two or more channels each for conducting a portion of fluid from the puncture wound; and (b) one or more lancets positioned near the plate unit associated therewith for passing through the one or more openings to puncture the skin when pressed into the skin;

wherein the plate unit comprises a first channel for conducting away a first portion of the fluid and a second channel for conducting a second portion of the fluid.

* * * * *